US006262115B1

(12) United States Patent
Guittard et al.

(10) Patent No.: US 6,262,115 B1
(45) Date of Patent: *Jul. 17, 2001

(54) METHOD FOR THE MANAGEMENT OF INCONTINENCE

(75) Inventors: George V. Guittard, Cupertino; Francisco Jao; Susan M. Marks, both of San Jose; David J. Kidney, Palo Alto; Fernando E. Gumucio, San Jose, all of CA (US)

(73) Assignee: ALZA Coporation, Mountain View, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/280,309

(22) Filed: Mar. 29, 1999

Related U.S. Application Data

(63) Continuation-in-part of application No. 08/806,773, filed on Feb. 26, 1997, now Pat. No. 5,912,268, which is a continuation-in-part of application No. 08/706,576, filed on Sep. 5, 1996, now Pat. No. 5,840,754, which is a continuation-in-part of application No. 08/445,849, filed on May 22, 1995, now Pat. No. 5,674,895.

(51) Int. Cl.$^7$ .................................................. A01N 37/44
(52) U.S. Cl. .......................... 514/534; 424/464; 424/468; 424/474; 424/475; 424/479; 424/480; 424/484; 424/486; 424/488
(58) Field of Search .................... 514/534; 424/464, 424/468, 474, 475, 479, 480, 484, 486, 488

(56) References Cited

U.S. PATENT DOCUMENTS

| | | |
|---|---|---|
| 2,799,241 | 7/1957 | Wurster . |
| 3,811,444 | 5/1974 | Heller et al. ........................ 128/260 |
| 3,845,770 | 11/1974 | Theeuwes et al. .................. 128/260 |
| 3,916,899 | 11/1975 | Theeuwes et al. .................. 128/260 |
| 3,962,414 | 6/1976 | Michaels ............................. 424/19 |
| 3,992,518 | 11/1976 | Chien et al. ......................... 424/22 |
| 4,063,064 | 12/1977 | Saunders et al. ................... 219/121 |
| 4,066,747 | 1/1978 | Capozza ............................... 424/78 |
| 4,070,347 | 1/1978 | Schmitt .............................. 260/77.5 |
| 4,079,038 | 3/1978 | Choi et al. ........................ 260/47 X |
| 4,083,949 | 4/1978 | Benedict ............................. 424/19 |
| 4,088,864 | 5/1978 | Theeuwes et al. .................. 219/121 |
| 4,093,709 | 6/1978 | Choi et al. ........................... 424/19 |
| 4,200,098 | 4/1980 | Ayer et al. ......................... 128/260 |
| 4,285,987 | 8/1981 | Ayer et al. ........................... 427/3 |
| 4,327,725 | 5/1982 | Cortese et al. .................... 128/260 |
| 4,434,153 | 2/1984 | Urquhart et al. .................... 424/22 |
| 4,612,008 | 9/1986 | Wong et al. ....................... 604/892 |
| 4,721,613 | 1/1988 | Urquhart et al. .................... 424/19 |
| 4,783,337 | 11/1988 | Wong et al. ....................... 424/468 |
| 4,816,263 | 3/1989 | Ayer et al. ........................ 424/468 |
| 4,853,229 | 8/1989 | Theeuwes ......................... 424/455 |
| 4,863,456 | 9/1989 | Stephens et al. ................ 604/892.1 |
| 4,902,514 | 2/1990 | Barclay et al. .................... 424/473 |
| 5,399,359 | 3/1995 | Baichwal ........................... 424/464 |
| 5,674,895 | * 10/1997 | Guittard et al. ................... 514/534 |
| 5,811,126 | 9/1998 | Krishnamurthy .................. 424/498 |
| 5,840,754 | * 11/1998 | Guittard et al. ................... 514/534 |
| 5,912,268 | * 6/1999 | Guittard et al. ................... 514/534 |

FOREIGN PATENT DOCUMENTS

| | | |
|---|---|---|
| WO 96/12477 | 5/1996 | (WO) . |
| WO 96/37202 | 11/1996 | (WO) . |

OTHER PUBLICATIONS

Lu, S.M., Yu, YJ.–Y., Inter. J. of Pharm. by Lu, vol. 112, pp. 117–124 (1994).
J. Pharm. Sci, by Fincher, vol. 57, pp. 1825–1835 (1968).
Pharm. Sci., by Remington, 17$^{th}$ Ed., Chp. 90, pp. 1603–1625 (1985), published by Mack Publishing.
Controlled Release of Drugs, by M. Rosoff, Chp. 2, pp. 53–95 (1989).
Polymers, by Coleman, et al., vol. 31, pp. 1187–1231 (1990).
Drug Carrier Systems, by Roerdink et al., vol. 9, pp. 57–109 (1989).
Adv. Drug Delivery Rev., by Leong et al., vol. 1, pp. 199–233 (1987).
Handbook of Common Polymers, Compiled by Roff et al., (1971), published by CRC Press.
J. Am. Pharm. Assoc., vol. 48, pp. 451–454 (1959); and ibid, vol. 49, pp. 82–84 (1960).
Modern Plastics Encyclopedia, vol. 46, pp. 62–70 (1969).
Pharm. Sci., by Remington, 14$^{th}$ Ed., pp. 1626–1680 (1970), published by Mack Publishing Co.
The United States Pharmacopoeia, The National Formulary, pp. 1791–1796 (1995).
Pharm. Sci., by Remington, 17$^{th}$ Ed., pp. 653–666 (1985).
USP XXII, Dissolution Paddle Analysis, pp. 1578–1579 (1990).
Database WPI, Derwent Publication Ltd., London, GB, AN 94–031722, XP002096607.
Database WPI, Derwent Publication Ltd., London, GB, AN 94–068306, XP002096606.
Gupta S.K. et al: "Evidence for Site–specific Presystemic Metabolism of Oxybutynin Following Oral Administration". Clinical Pharmacology & Therapeutics, vol. 61, No. 2, 1997, p. 227 XP002099744.
Nilsson C.G. et al: "Comparison of a 10–mg Controlled Release Oxybutynin Tablet With a 5–mg Oxybutynin Tablet in Urge Incontinent Patients" Neurology and Urodynamics, vol. 16, No. 6, 1997, pp. 533–542 XP002099745.

* cited by examiner

*Primary Examiner*—Michael A. Williamson
(74) *Attorney, Agent, or Firm*—John A. Dhuey; Steven F. Stone

(57) ABSTRACT

A composition and a dosage form are disclosed comprising oxybutynin alone/or accompanied by another drug indicated for therapy. A method is disclosed for administering oxybutynin alone/or accompanied by a different drug or for administering oxybutynin and a different drug according to a therapeutic program for the management of incontinence alone, and for other therapy.

31 Claims, No Drawings

METHOD FOR THE MANAGEMENT OF INCONTINENCE

CROSS-REFERENCE TO RELATED APPLICATION

This application is a continuation-in-part of U.S. patent application, Ser. No. 08/806,773 filed Feb. 26, 1997, now U.S. Pat. No. 5,912,268 issued Jun. 15, 1999, which application is a continuation-in-part of U.S. patent application Ser. No. 08/706,576 filed Sep. 5, 1996, now U.S. Pat. No. 5,840,754 issued Nov. 24, 1998, which is a continuation-in-part of U.S. patent application Ser. No. 08/445,849 filed May 22, 1995, now U.S. Pat. No. 5,674,895 issued Oct. 7, 1997, benefit is claimed of these applications, that are assigned to the ALZA Corporation of Palo Alto, Calif.

FIELD OF THE INVENTION

This invention pertains to the management of incontinence. More specifically the invention relates to the management of incontinence by administering to a patient having the symptoms of incontinence a therapeutically effective dose of oxybutynin alone, in combination with another drug, proceeded by the administration of another drug, or followed by the administration of another drug.

BACKGROUND OF THE INVENTION

Many people are affected by urinary incontinence. Incontinence is particularly common in the elderly, urinary incontinence is present in approximately fifty percent of nursing home patients, and urinary incontinence is a well known urologic problem in women. It will affect nearly all women in some form during their lifetime, and it is of significant medical and social concern to all humans who experience it. Urinary incontinence arises from the anatomy and from the physiology of the urinary tract, which is composed of a bladder and a sphincter. Anatomically, the bladder consists of the bladder musculature, also known as detrusor, and the trigone. The sphincter includes the bladder neck and the proximal urethra. The detrusor muscle is innervated by the pelvic nerve through the parasympathetic nervous system, and the bladder neck and proximal urethra are innervated by the sympathetic nervous system.

The major functions of the bladder are the storage and expulsion of urine. The bladder is responsible for accommodating increasing volumes of urine at low pressures. Normally, the bladder remains closed during bladder filling and continence is maintained as long as the bladder neck and urethral pressure exceeds intravesical pressure. Voluntary voiding occurs when intravesical pressure exceeds bladder neck and urethral pressure, and involuntary voiding also known as involuntary incontinence occurs when the travesical pressure exceeds the bladder neck and urethral pressure. Involuntary incontinence also known as urge incontinence and overactive bladder, occurs with a loss of a large volume of urine accompanied by symptoms of urgency, frequency and nocturia caused by an unstable bladder or detrusor instability. The patient may lose urine with a change in position or with auditory stimulation. The loss of small volumes of urine usually occurs because bladder over distension by a large amount of residual urine referred to as overflow incontinence. Urinary incontinence is also known as overactive bladder with symptoms of urinary frequency or urge incontinence.

The present management of incontinence consists in administering a smooth muscle relaxant, such as oxybutynin, which acts directly on the smooth muscle at the site distal to the cholinergic receptor. The prior art administered oxybutynin alone for this stated therapeutic purpose. The prior art usual dose for the pharmacologic management of incontinence is repeated, nonsustained and noncontrolled doses from two-to-four times a day for oxybutynin. The prior art administered separately the steriods, estrogen and/or progesterone hormone replacement therapy however, this steroid therapy is insufficient for the management of incontinence.

In light of the above presentation it will be appreciated by those versed in the medical and pharmaceutical dispensing arts to which this invention pertains that a pressing need exists for a therapeutic method that can deliver the therapeutic drug oxybutynin in a controlled, sustained-extended dose to a patient in clinical need of incontinence management. The pressing need exists for an oral method of therapy that can deliver oxybutynin alone at a substantially sustained release constant dose per unit time for its therapeutic effect. The need exists additionally for a method for delivering a dose of oxybutynin once-a-day, when indicated, for its intended therapy while avoiding an overdose and for lessening the side effects that can accompany the drug. The pressing need exists further for a method that can administer oxybutynin in combination with another and different drug, or in different therapeutic programs for the management of incontinence and for the management of health and disease.

It will be appreciated by those skilled in the medical and pharmaceutical arts to which this invention pertains, that if a novel and unique method of administration is made available that delivers oxybutynin alone, or in combination with another drug in a therapeutically effective dose over a sustained time for the management of incontinence, while lessening the incidence of over and under dose, such a method of therapy would represent an advancement and a valuable contribution for providing practical therapy.

SUMMARY OF THE INVENTION

According to the invention, it is an object of the invention to provide a method for the management of urinary incontinence with oxybutynin and/or its pharmaceutically acceptable salt alone, or in combination with another drug, or preceeded by or followed by the administration of another drug, for the management of incontinence in human male and female patients. The object of the invention further comprises a method for administering oxybutynin alone, and/or in combination with or preceded by or followed by an estrogen and/or a progestin for treating urinary incontinence in pregnant, nonpregnant, postpartum, menopause, post menopausal, and during climaterix period of change occurring in the transition to menopause in a patient in need of therapy.

DETAILS OF THE INVENTION

The scientific terms and scientific phrases used in this specification embrace the following definitions: Dosage form denotes a drug delivery system for administering a therapeutically effective dose of drug, for example oxybutynin to a patient in need of therapy. The dosage form may be administered once-daily, that is, as a once-a-day dosage form for increasing patient compliance for treating overactive bladder, or more frequently as indicated by a physician, for example twice-daily or thrice-daily. Sustained release denotes the constant delivery of drug for up to twenty-hours. Controlled release denotes the delivery of the drug at a rate controlled by a dosage form by the method of the invention.

Zero-order release denotes the method of delivery of drug at a uniform rate to dampen the peaks and valleys observed in non-zero order method of drug delivery. Therapeutically effective amount denotes the dose of delivered drug sufficient to provide a local or a systemic effect in a patient. Menopause denotes the period of natural cessation of menstruation in the female. Post menopausal denotes the time occurring after menopause. Pregnancy denotes the state of containing an unborn fetus within the female. Postpartum denotes the period following birth.

The present invention provides a therapeutic composition comprising 240 ng to 650 mg (nanogram to milligrams) of oxybutynin or an oxybutynin therapeutically acceptable salt. The pharmaceutically acceptable salt is selected from the group consisting of acetate, bitartrate, citrate, edetate, chloride, edisylate, estolate, esylate, fumarate, gluceptate, gluconate, glutamate, hydrobromide, hydrochloride, lactate, malate, maleate, mandelate, mesylate, methylnitrate, mucate, napsylate, nitrate, pamoate, pantothenate, phosphate, salicylate, stearate, succinate, sulfate, tannate, and tartrate. The drug oxybutynin can be present as the racemate, as the R-enantiomer or as the S-enantiomer. The oxybutynin and its pharmaceutically acceptable salt can be administered at a controlled mean release rate of 0.10 ng per hour to 25 mg per hour for the management of incontinence up to 24 hours. The dosage forms provided by the invention can administer oxybutynin in doses such as 5 mg, 10 mg, 15 mg, 20 mg etc. for the management of incontinence. The oxybutynin can be administered alone, or in therapeutic programs with another and different drug, from the same dosage form or from different dosage forms.

Representative of a drug, for example a steroid, that can be administered with prior to or followed by the administration of oxybutynin, according to the method of the invention in the same or in an accompanying method, at the same or at a different time, or the drug can be administered separately within up to twenty-four hour period comprise a progestin member selected from the group consisting of progesterone, medroxyprogesterone, medroxyprogestrone acetate, hydroxyprogesterone, hydroxyprogesterone caproate, norethindrone, norethindrone acetate, megestrol, megestrol acetate, progestin, progestogin, norgestrel, norethisterone, norethisterone acetate, levonorgestrel, norgestimate, norethynodrel, 17-hydroxyprogesterone esters, 19-nor-17-hydroxyprogesterone, 19-nor-17-hydroxyprogesterone esters, 17α-ethinyltestosterone, 17α-ethinyl-19-nor-testosterone, d-17β-acetoxy-13β-ethyl-17α-ethinyl-17β-hydroxygon-4-en-3-one, 13β-ethyl-17β-hydroxygon-4-en-3-one, 13β-17α-diethyl-17β-hydroxygon-4-en-3-one, chlormadione acetate, dimethistrone, 17α-ethinyl-β-acetoxy-19-norandrost-4-en-3-one oxime, 3-ketodesogestrel, desogestrel, gestodene, and gestodene acetate. The dose of the progestin and its progrestone derivatives administered is 10 ng to 600 mg, that is administered alone, or in combination with an estrogen, and is indicated for hormone replacement therapy.

Representative of a drug that can be administered with oxybutynin according to the method of the invention, or administered separately in a separate administration in twenty-four hours include an estrogen steroid possessing estrogenic activity selected from the group consisting estradiol, estradiol valerate, estradiol benzoate, estradiol cypionate, estradiol propionate, estradiol dipropionate, estradiol acetate, ethinyl estradiol, 17α-ethinyl estradiol-esters, 17α-ethinyl estradiol acetate, 17α-ethinyl estradiol benzoate, 17α-ethinyl estradiol ethers, estrone, estrone acetate, estrone sulfate, estriol, estriol succinate, estriol triacetate, conjugated equine estrogens, and estradiol esters. The dose of estrogen and its estrogen derivatives is 10 ng to 600 mg, that is administered alone, or in combination with a progestin for hormone replacement therapy.

Representative of progestin and estrogen combination that can be administered according to the methods of this invention comprise a hormone pair selected from the group consisting of progestin and estradiol valerate, progestin and piperazine estrone, progestin and estrone, progestin and estriol, progestin and conjugated equine estrogens, progesterone and estradiol, progesterone and estrone, progesterone and estriol, progesterone and conjugated equine estrogens, norethisterone and estradiol, medoxyprogesterone and estradiol, norgestrel and estradiol, dyhrogesterone and estrogen, progestrone and estrogen sulfate, progesterone and 17α-dihydroequilin, and progesterone and equilenin.

The method of the invention provides oxybutynin and the steroids can be administered from the same dosage form, or the oxybutynin and the steroids can be administered separately from different dosage forms, with in either administrations, the oxybutynin and the steroids, in one present administration, administered within a twenty-four therapeutic period.

The method of the invention further provides delivery means for administering oxybutynin at a rate conducive for lessening the conversion of oxybutynin at least in part to the desethyl metabolite, desoxy. The method provides for the controlled and sustained rate at which oxybutynin is delivered to the plasma to lessen the circulating desoxy metabolite and to reduce side effect associated therewith. The method provides for oxybutynin delivery to a patient at a rate which gives an oxybutynin/desoxy metabolite ratio higher than 0.18:1 and/or the plasma level of the desoxy metabolite do not exceed 350 ng•h/ml, to lessen side effects. According to this feature of the invention there is provided a desethyl metabolite of α-cyclohexyl-α-hydroxy-benzeneacetic acid-4-(diethyl amino)-2-butynyl ester, or its pharmaceutically acceptable salt so the desethyl metabolite does not exceed 350 ng•h/ml, and may even exhibit peak levels of 250 or 200 ng•h/ml.

The method for delivering oxybutynin neat, and/or other drugs according to the invention comprises, in one manufacture the use of drug releasing beads that on dissolution or diffusion release the drug over 24 hours. The drug releasing beads comprise a central composition or core comprising a drug and pharmaceutically acceptable composition forming ingredients including an optional lubricant, antioxidant, and buffer. The beads are medical preparations with a general diameter of 1 mm to 2 mm. The beads comprise doses of drug, for example, 1 mg, 2 mg, 10 mg, and 20 mg, increasing up to 40 mg. The beads in an embodiment are formed of noncrossed-linked materials to enhance their discharge from the gastrointestional tract. The beads are coated with a release rate controlling polymer that give a timed released profile. The timed release beads are manufactured into a tablet for therapeutically effective drug administration. The beads are made into matrix tablets by the direct compression of a plurality of beads coated with, for example, an acrylic resin and blended with excipients such as hydroxypropyl-methylcellulose. The manufacture of beads is disclosed in *Inter. J. of Pharm.*, by Lu, Vol.112, pp. 117–124 (1994); *Pharm. Sci.*, by Remington, 14$^{th}$ Ed. pp. 1626–1628 (1970); *J. Pharm. Sci.*, by Fincher, Vol. 57, pp. 1825–1835 (1968); and U.S. Pat. No. 4,083,949. The manufacture of the tablet is described in *Pharmaceutical Sciences*, by Remington, 17$^{th}$ Ed., Chp. 90, pp. 1603–1625, (1985), published by Mack Publishing Co., Easton, Pa.

The method for delivering oxybutynin alone, or in combination with another drug comprises in another embodiment the use of oxybutynin coated on a polymer substrate. The polymer can be an erodible, or a nonerodible polymer. The coated substrate is folded onto itself to provide a bilayer polymer drug dosage form. For example, 1 ng to 40 mg oxybutynin alone, or in combination with an estrogen, or in combination with an estrogen-progestin pair is coated onto a polymer such as a polypeptide, collagen, gelatin, polyvinyl alcohol, polyorthoester, polyacetyl, or a polyorthocarbonate, and the coated polymer folded onto itself to provide a bilaminated dosage form. In operation, the bioerodible dosage form erodes at a controlled rate to dispensed a therapeutic dose of oxybutynin alone, or oxybutynin and a steroid pair over a sustained release period. Representative biodegradable polymer comprise a member selected from the group consisting of biodegradable poly(amides), poly (amino acids), poly(esters), poly(lactic acid), poly(glycolic acid), poly(carbohydrate), poly(orthoester), poly (orthocarbonate), poly(acetyl), poly(anhydrides), biodegradable poly(dehydropyrans), and poly(dioxinones). The polymers are known to the art in *Controlled Release of Drugs*, Rosoff, Chp. 2, pp. 53–95 (1989); and in U.S. Pat. Nos. 3,811,444; 3,962,414; 4,066,747, 4,070,347; 4,079,038; and 4,093,709.

The method of the invention further uses a dosage form comprising a polymer that releases a drug by diffusion through a polymer, or by flux through pores, or by rupture of a polymer matrix. The drug delivery polymeric dosage form comprises a concentration of 10 ng to 250 mg homogenously contained in or on a polymer. The dosage form comprises at least one exposed surface at the beginning of dose delivery. The nonexposed surface when present is coated with a pharmaceutically acceptable material impermeable to the passage of drug. The dosage form can be manufactured by procedures known to the prior art. An example of providing a dosage form comprises blending a pharmaceutically acceptable carrier, like polyethylene glycol, with a known dose of oxybutynin alone, or oxybutynin and an estrogen, at an elevated temperature, like 37° C., and adding it to a silastic medical grade elastomer with a cross-linking agent, for example, octanoate, followed by casting in a mold. The step is repeated for each optional successive layer. The system is allowed to set, for 1 hour, to provide the dosage form. Representative polymers for manufacturing the dosage form comprise a member selected from the group consisting of olefin and vinyl polymers, addition polymers, condensation polymers, carbohydrate polymers, and silicon polymers as represented by poly (ethylene), poly(propylene), poly(vinyl acetate), poly (methyl acrylate), poly(isobutyl methacrylate), poly (alginate), poly(amide), and poly(silicone). The polymers and manufacturing procedures are known in *Polymers*, by Coleman et al., Vol. 31, pp. 1187–1231 (1990); *Drug Carrier Systems*, by Roerdink et al., Vol. 9, pp. 57–109 (1989); *Adv. Drug Delivery Rev.*, by Leong et al., Vol. 1, pp. 199–233 (1987); *Handbook of Common Polymers*, Compiled by Roff et al., (1971), published by CRC Press; and U.S. Pat. No. 3,992,518.

The method of the invention also uses a dosage form comprising a matrix comprising a plurality of tiny pills. The timed released tiny pills provide a number of individual doses for providing various timed doses for achieving a sustained-release drug delivery profile over 24 hours. The matrix comprises a hydrophilic polymer selected from the group consisting of a polysaccharide, agar, agarose, natural gum, alkali alginate including sodium alginate, carrageenan, fucoidan, furcellaran, laminaran, hypnea, gum arabic, gum ghatti, gum karaya, grum tragacanth, locust bean gum, pectin, amylopectin, gelatin, and a hydrophilic colloid. The hydrophilic matrix comprises a plurality of 4 to 50 tiny pills, each tiny pill comprising a dose population of from 10 ng, 0.5 mg, 1 mg, 1.2 mg, 1.4 mg, 1.6 mg, 5.0 mg, etc. The tiny pills comprise a release rate controlling wall of 0.001 up to 10 mm thickness to provide for the timed release of drug. Representative of wall-forming materials include a triglyceryl ester selected from the group consisting of glyceryl tristearate, glyceryl monostearate, glyceryl dipalimitate, glyceryl laureate, glyceryl didecenoate and glyceryl tridenoate. Other wall forming materials comprise polyvinyl acetate phthalate, methylcellulose phthalate, and microporous vinyl olefins. Procedure for manaufacturing tiny pills are disclosed in U.S. Pat. Nos. 4,434,153; 4,721,613; 4,853,229; 2,996,431; 3,139,383, and 4,752,470.

The method of the invention also comprises administering orally to a human patient a dosage form comprising a semipermeable wall that surrounds a therapeutic composition comprising oxybutynin. In use within a patient, the osmotic dosage form comprising a homogenous composition imbibes fluid through the semipermeable wall into the dosage form in response to the concentration gradient across the semipermeable wall. The therapeutic composition in the dosage form develops osmotic energy that causes the therapeutic composition to be administered through an exit from the dosage form over a prolonged period of time up to 24 hours (or even in some cases up to 30 hours) to provide controlled and sustained oxybutynin therapy. The method of the invention also uses in another embodiment an osmotic dosage form comprising a wall surrounding a compartment, the wall comprising a semipermeable polymeric composition permeable to the passage of fluid and substantially impermeable to the passage of oxybutynin present in the compartment; an oxybutynin drug layer composition in the compartment comprising the oxybutynin; a hydrogel push layer composition in the compartment comprising an osmotic formulation for imbibing and absorbing fluid for expanding in size for pushing the oxybutynin composition layer from the dosage form; and at least one passageway in the wall for releasing the oxybutynin. The method delivers the oxybutynin, alone or in combination with a steroid by imbibing fluid through the semipermeable wall at a fluid imbibing rate determined by the permeability of the semipermeable wall and the osmotic pressure across the semipermeable wall causing the push layer to expand; and thereby deliver the therapeutically active oxybutynin from the dosage form through the exit passageway to a patient over a prolonged period of time up to 24 or even 30 hours. The oxybutynin administered by the dosage form of the invention is in the therapeutic range that avoids a toxic dose and avoids an ineffective dose for antispasmodic therapy. The oxybutynin may thus be administered by the methods of this invention to patients with uninhibited neurogenic and reflex neurogenic bladder for increased vessel capacity which diminishes the frequency of uninhibited contractions of the detrusor muscle and delays the desire to void. The dosage form is indicated for the relief of symptoms associated with voiding such as urgency, urge incontinence, frequency, nocturia and incontinence in patients in neurogenic bladder. The dosage form can be used also for human hormone replacement therapy as described above.

The osmotic dosage forms in one manufacture comprise a therapeutic composition comprising 240 ng to 650 mg of a member selected from the group consisting of oxybutynin and its pharmaceutically acceptable salt, from 10 mg to 350 mg of a pharmaceutically acceptable hydrogel such as a polyalkylene oxide of 75,000 to 750,000 weight-average molecular weight. Representative of polyalkylene oxides are polyethylene oxide of 100,000 weight-average molecular weight, polyethylene oxide of 200,000 weight-average molecular weight, polyethylene oxide of 300,000 weight-average molecular weight, polyethylene oxide of 600,000 weight-average molecular weight, and polypropylene oxide of 100,000 weight average molecular weight. The therapeutic composition may also comprise 0 mg to 50 mg, in a present manufacture 1 mg to 50 mg of a hydroxypropylalkylcellulose of 9,000 to 150,000 average-number molecular weight selected from the group consisting of hydroxypropylmethylcellulose, hydroxypropylethylcellulose, hydroxypropylbutylcellulose, and hydroxypropylpentylcellulose, 0 to 20 mg of a hydroxyalkylcellulose, such as hydroxypropylcellulose; 0 mg to 50 mg, in a present manufacture 1 mg to 50 mg, of an osmotic solute selected from the osmotically effective compounds consisting of sodium chloride, potassium chloride, potassium acid phosphate, tartaric acid, citric acid, raffinose, magnesium sulfate, magnesium chloride, urea, inositol, sucrose, glucose and sorbitol; and 0.00 mg to 7.5 mg and one manufacture 0.01 mg to 5 mg of a lubricant, such as calcium stearate, zinc stearate, magnesium stearate, magnesium oleate, calcium palmitate, sodium suberate, potassium laureate, salts of fatty acids, salts of alicyclic acids, salts of aromatic acids, stearic acid, oleic acid, palmitic acid, and a mixture of salt of fatty, alicyclic or aromatic acid and a fatty, alicyclic or aromatic acid.

The invention provides for the therapeutic composition comprising the drug oxybutynin to be administered as the composition neat, that is, oxybutynin alone, for increasing the urinary bladder capacity, for diminishing the frequency of uninhibited contractions of the detrusor muscles and its accompanying delay of the desire to void. The invention provides for the therapeutic oxybutynin composition to be surrounded by a wall comprising a semipermeable composition with an exit for delivering the therapeutic composition to a human patient in need of oxybutynin therapy. The invention provides, in an additional embodiment, the therapeutic composition comprising oxybutynin as a therapeutic layer in layered, contacting arrangement with a hydrogel expansion composition manufactured as a layer that supports the therapeutic composition to yield a bilayered matrix. The hydrogel layer composition may comprise 10 mg to 350 mg of a hydrogel, such as a member selected from the group consisting of a polyalkylene oxide of 1,000,000 to 8,000,000 which are selected from the group consisting of polyethylene oxide of 1,000,000 weight-average molecular weight, a polyethylene oxide of 2,000,000 molecular weight, a polyethylene oxide of 4,000,000 molecular weight, a polyethylene oxide of 5,000,000 molecular weight, a polyethylene oxide of 7,000,000 molecular weight, and a polypropylene oxide of the 1,000,000 to 8,000,000 weight-average molecular weights; or 10 mg to 250 mg of an alkali carboxymethylcellulose of 10,000 to 6,000,000 weight-average molecular weight such as sodium carboxymethylcellulose or potassium carboxymethylcellulose. The hydrogel expansion layered comprises 0.0 mg to 350 mg, in present manufacture 0.1 mg to 250 mg of a hydroxyalkylcellulose of 7,500 to 4,500,000 weight-average molecular weight, represented by hydroxymethylcellulose, hydroxyethylcellulose, hydroxypropylcellulose, hydroxybutylcellulose, and hydroxypentylcellulose; 0 mg to 50 mg, in present manufacture 1 mg to 50 mg of an osmagent selected from the group consisting of sodium chloride, potassium chloride, potassium acid phosphate, tartaric acid, citric acid, raffinose, magnesium sulfate, magnesium chloride, urea, inositol, sucrose, glucose and sorbitol; 0 to 5 mg of a colorant, such as ferric oxide; 0 mg to 30 mg, in a present manufacture, 0.1 mg to 30 mg of a hydroxypropylalkylcellulose of 9,000 to 225,000 average-number molecular weight, selected from the group consisting of hydroxypropylethylcellulose, hydroxypropypentylcellulose, hydroxypropylmethylcellulose, and hydropropylbutylcellulose; 0.00 to 1.5 mg of an antioxidant selected from the group consisting of ascorbic acid, butylated hydroxyanisole, butylatedhydroxyquinone, butylhydroxyanisol, hydroxycomarin, butylated hydroxytoluene, cephalm, ethyl gallate, propyl gallate, octyl gallate, lauryl gallate, propylhyd roxybenzoate, trihydroxybutylrophenone, dimethylphenol, dibutylphenol, vitamin E, lecithin and ethanolamine; and 0.0 mg to 7 mg of a lubricant selected from the group consisting of calcium stearate, magnesium stearate, zinc stearate, magnesium oleate, calcium palmitate, sodium suberate, potassium laureate, salts of fatty acids, salts of alicyclic acids, salts of aromatic acids, stearic acid, oleic acid, palmitic acid, a mixture of a salt of a fatty, alicyclic or aromatic acid, and a fatty, alicyclic, or aromatic acid.

The invention provides for the therapeutic oxybutynin composition, the therapeutic bilayer comprising the drug oxybutynin layer, and the osmopolymer hydrogel layer to be administered as the composition or the bilayer per se; that is, as the composition or the bilayer together for increasing the urinary bladder capacity, for diminishing the frequency of uninhibited contractions of the detrusor muscles and its accompaying delay of the desire to void. The invention provides additionally for the therapeutic composition and for the compositional bilayer to be surrounded by a wall comprising a semipermeable composition with an exit for delivering the therapeutic composition to a human patient in need of oxybutynin therapy. The invention also provides for a subcoat to surround the therapeutic composition or to surround the bilayer, which subcoat in either embodiment is surrounded by a outer semipermeable wall.

The invention provides a dosage form for the delivery of the therapeutic composition comprising oxybutynin. The dosage form comprises up to 650 mg, and provides a sustained release at a controlled rate up to 25 mg, of oxybutynin or its salt up to 24 hours. The dosage form comprises a wall, which wall surrounds an internal lumen or compartment. The wall comprises a semipermeable composition that is permeable to the passage of fluid and impermeable to the passage of oxybutynin. The wall is nontoxic and it comprises a polymer selected from the group consisting of a cellulose acylate, cellulose diacylate, cellulose triacylate, cellulose acetate, cellulose diacetate and cellulose triacetate. The wall comprises 75 wt % (weight percent) to 100 wt % of the cellulosic wall-forming polymer; or, the wall can comprise additionally 0.01 wt % to 80 wt % of polyethylene glycol, or 1 wt % to 25 wt % of a cellulose ether selected from the group consisting of hydroxypropylcellulose or hydroxypropylalkycellulose such as hydroxypropylmethylcellulose. The total weight percent of all components comprising the wall is equal to 100 wt %. The internal compartment comprises the therapeutic oxybutynin composition alone or in layered position with an expandable hydrogel composition. The expandable hydrogel composition in the compartment increases in dimension by imbibing the fluid through the semipermeable wall, causing the hydrogel to expand and occupy space in the compartment, whereby the drug composition is pushed from the dosage form. The therapeutic layer and the expandable layer act together during the operation of the dosage form for the release of oxybutynin to a patient over time. The dosage form comprises a passageway in the wall that connects the exterior of the dosage form with the internal compartment. The osmotic powered dosage form provided by the invention delivers oxybutynin from the dosage form to the patient at a zero order rate of release over a period of 24 hours.

The expression "passageway" as used herein comprises means and methods suitable for the metered release of the therapeutic drug from the compartment of the dosage form. The exit means comprises at least one passageway, including orifice, bore, aperture, pore, porous element, hollow fiber, capillary tube, channel, porous overlay, or porous element that provides for the osmotic controlled release of oxybutynin. The passageway includes a material that erodes or is leached from the wall in a fluid environment of use to produce at least one controlled-release dimensioned passageway. Representative materials suitable for forming a passageway, or a multiplicity of passageways comprise a leachable poly(glycolic) acid or poly(lactic) acid polymer in the wall, a gelatinous filament, poly(vinyl alcohol), leachable polysaccharides, salts, and oxides. A pore passageway, or more than one pore passageway, can be formed by leaching a leachable compound, such as sorbitol, from the wall. The passageway possesses controlled-release dimensions, such as round, triangular, square and elliptical, for the metered release of oxybutynin from the dosage form. The dosage form can be constructed with one or more passageways in spaced apart relationship on a single surface or on more than one surface of the wall. The expression "fluid environment" denotes an aqueous or biological fluid as in a human patient, including the gastrointestional tract. Passageways and equipment for forming passageways are disclosed in U.S. Pat. Nos. 3,845,770; 3,916,899; 4,063,064; 4,088,864 and 4,816,263. Passageways formed by leaching are disclosed in U.S. Pat. Nos. 4,200,098 and 4,285,987.

DESCRIPTION FOR MANUFACTURING THE COMPOSITIONS AND DOSAGE FORMS OF THE INVENTION

The wall of dosage forms can be formed by using an air suspension procedure. This procedure consists of suspending and tumbling the composition or the layers in a current of air and wall-forming composition until a wall is applied to the oxybutynin forming compartment. The air suspension procedure is well suited for independently forming the wall. The air suspension procedure is described in U.S. Pat. No. 2,799,241; *J. Am. Pharm. Assoc.*, Vol. 48, pp. 451–454 (1959); and ibid, Vol. 49, pp. 82–84 (1960). The wall can be formed with a wall-forming composition in a Wurster® air suspension coater using an organic solvent, such as acetone-water cosolvent 90:10 (wt:wt) with 2.5 wt % to 7 wt % polymer solids. An Aeromatic® air suspension coater using, for example, a methylene dichloride-methanol cosolvent comprising 87:13 (v:v) can be used for applying the wall. Other wall-forming techniques, such as pan coating system, wall forming compositions deposited by successive spraying of the composition or the bilayered arrangement, accompanied by tumbling in a rotating pan can be used for the present purpose. A larger volume of cosolvent can be used to reduce the concentration of polymer solids to produce a thinner wall. Finally, the wall of the coated compartments are laser or mechanically drilled, and then dried in a forced air or humidity oven for 1 to 3 days or longer to free the solvent. Generally, the walls formed by these techniques have a thickness of 2 to 20 mils (0.051 to 0.510 mm) with a preferred thickness of 2 to 6 mils (0.051 to 0.150 mm).

The dosage forms of the invention are manufactured by standard manufacturing techniques. For example, in one manufacture the beneficial drug oxybutynin and/or additional drugs such as an estrogen, a steroid pair such as an estrogen and a progestin, and other ingredients comprising a therapeutic composition or comprising the drug composition that faces the exit means are blended, or they are blended then pressed into a composition. The oxybutynin and other ingredients can be blended with a solvent and then formed into a solid or semisolid formed by conventional manufacturing methods such as ball-milling, calendaring, sitrring, or roll-milling and then pressed into a selected shape. The composition possesses dimensions that correspond to the internal dimensions of the area it occupies in the dosage form. In the manufacture of bilayered compositions dosage form, the bilayers posses dimensions corresponding to the internal lumen of the dosage form. First, the hydrogel expansion layer is placed in contact with the oxybutynin layer. The layering of the oxybutynin layer and the hydrogel layer can be fabricated by conventional press-layering techniques. Finally, the two-layer compartment forming members are surrounded and coated with an outer wall. A passageway is drilled by laser or mechanically drilled through the wall, or the wall is provided with a pore-former to contact the oxybutynin layer, with the dosage form optically oriented automatically by the equipment for laser forming the passageway on the preselected drug surface.

In another manufacture, the dosage forms are manufactured by the wet granulation technique. In the wet granulation technique the oxybutynin and/or other drugs, and the ingredients comprising the drug composition are blended using an organic or inorganic solvent, such as isopropyl alcohol-methylene dichloride 80:20 (v:v) as the granulation fluid. Other granulating fluid, such as water, isopropyl alcohol, or denatured alcohol 100% can be used for this to purpose. The ingredients forming the drug composition are individually passed through a 40 mesh screen and then thoroughly blended in a mixer. Next, other ingredients comprising the drug composition are dissolved in a portion of the granulation fluid, such as the cosolvent described above. Then, the latter prepared wet blend is slowly added to the drug oxybutynin blend with continual mixing in the blender. The granulating fluid is added until a wet blend mass is produced, which wet mass is then forced through a 20 mesh screen onto oven trays. The blend is dried for 18 to 24 hours at 25° C. to 40° C. The dry granules are then screened with a 16 mesh screen. Next, a lubricant is passed through an 60 mesh screen and added to the dry screened granule blend. The granulation is put into milling jars and mixed on a jar mill for 2 to 10 minutes. The first and second layer compositions are pressed into a layered tablet, for example, in a Manesty® layer press.

Another manufacturing process that can be used for providing a oxybutynin and hydrogel composition comprises blending their powdered ingredients in a fluid bed granulator. After the powdered ingredients are dry blended in the granulator, a granulating fluid, for example, poly (vinylpyrrolidone) in a solvent, such as in water, is sprayed onto the respective powders. The coated powders are then dried in a granulator. This process coats the ingredients present therein while spraying the granulating fluid. After the granules are dried, a lubricant, such as stearic acid or magnesium stearate, is blended as above into the mixture. The granules are then pressed in the manner described above. In another embodiment, when the fluid bed granulating process is used to manufacture the hydrogel layer, the antioxidant present in the polyalkylene oxide can be removed during the processing step. If antioxidant is desired it can be added to the hydrogel formulation, and this can be accomplished during the fluid bed granulation process.

The dosage forms of this invention are manufactured in another embodiment by mixing the oxybutynin with composition-forming ingredients and pressing the composition into a layer possessing dimensions that correspond to the internal dimensions of the compartment space adjacent to a passageway. In another embodiment, the oxybutynin and other drug composition forming ingredients and a solvent are mixed into a solid, or semi-solid, by conventional methods such as ball-milling, calendaring, stirring or roll-milling, and then pressed into a preselected, layer-forming shape. The invention provides further a method of manufacturing a sustained release dosage form adapted for managing oxybutynin and its desethylmetabolite in plasma by incorporating an effective amount of oxybutynin or its salt in a controlled release dosage form that releases oxybutynin continuously at a controlled rate to provide a higher oxybutynin concentration and a lower desethylmetabolite concentration than provided by an immediate release dosage form that dose-dumps. An immediate release dosage form generally dose-dumps its drug in an hour or less, as it lack prolonged delivery.

In the manufactures as presented above, the manufacture comprising a composition or comprising a layer of a composition comprising a hydrogel osmopolymer and an optional osmagent are placed in contact with the layer comprising the drug oxybutynin, and the two layers comprising the layers are surrounded with a semipermeable wall. The layering of the first drug oxybutynin composition and the second hydrogel osmopolymer and optional osmagent composition can be accomplished by using a conventional two-layer tablet press technique. The wall can be applied by molding, spraying or dipping the pressed shapes into wall-forming materials. Another technique that can be used for applying the wall is the air suspension coating procedure. This procedure consists in suspending and tumbling the two layers in a current of air until the wall forming composition surrounds the layers. Manufacturing procedures are described in *Modern Plastics Encyclopedia*, Vol. 46, pp. 62–70 (1969); and in *Pharmaceutical Sciences*, by Remington, 14$^{th}$ Ed., pp. 1626–1680 (1970), published by Mack Publishing Co., Easton, Pa. The dosage form can be manufactured by following the teaching in U.S. Pat. Nos. 4,327,725; 4,612,008; 4,783,337; 4,863,456; and 4,902,514.

The dissolution of a drug indicates the drug entering into solution upon its delivery from a dosage form provided by this invention is measured by the following procedure. First, a drug receiving solution, such as, gastrointestinal fluid, hydrochloric acid, or an aqueous sodium dodecyl sulfate, 1% (w/v) (weight/volume) solution is used as the dissolution media. A dosage form prepared by this invention is placed into the dissolution media and the drug released by the dosage form into the dissolution media is sampled at a constant time interval over the time period of dissolution. The filtered samples are assayed by a reversed high pressure liquid chromatography, or detection by UV. The concentration of the samples is measured against a standard curve containing, for example, at least five standard points. Procedures for dissolution testing are reported in *The United States Pharmacopoeia*, The National Formulary, pp. 1791 to 1796; (1995); *Pharmaceutical Sciences*, by Remington, 17$^{th}$ Ed., pp. 653–666 (1985); and *USP XXII*, Dissolution Paddle Analysis, pp. 1578–1579 (1990).

The release rate of drug from a dosage form manufactured by this invention can be ascertained by the following procedure. The procedure comprises placing the dosage form in a solution, usually water, and taking aliquots of the release rate solution, followed by their injection into a chromatographic system to quantify the amount of drug released during specified test intervals. The drug, for example, is resolved on a column and detected by UV absorption. Quantitation is performed by linear regression analysis of peak areas from a standard curve containing at least five standard points.

The release rate procedure comprises attaching a dosage form to a plastic rod with the orifice exposed to the drug receiving solution. Then, attaching the rod to a release arm, with the arm affixed to an up/down reciprocating shaker, which operates at an amplitude of about 3 cm and 2 seconds per cycle. Then, continuously immersing the dosage form in 50 ml test tubes containing 30 ml of $H_2O$, equilibrated in a constant temperature water bath at 37° C.±0.5° C. Next, at the end of each interval, transfer the dosage form to the next row of new test tubes containing a receiving solution, such as water. After the release pattern is complete, remove the tubes and allow to cool to room temperature, followed by filling the calibrated tubes to the 50 ml mark with a solvent, such as acetone. The samples are mixed immediately, transferred to sample vials, followed by chromatography analysis.

Exemplary solvents suitable for manufacturing the wall, the composition layers and the dosage form include inert inorganic and organic solvents that do not adversely harm the materials, the wall, the layer, the composition and the drug wall. The solvents broadly include members selected from the group consisting of aqueous solvents, alcohols, ketones, esters, ethers, aliphatic hydrocarbons, halogenated solvents, cycloaliphatics, aromatics, heterocyclic solvents, and mixtures thereof. Typical solvents include acetone, diacetone alcohol, methanol, ethanol, isopropyl alcohol, butyl alcohol, methyl acetate, ethyl acetate, isopropyl acetate, n-butyl acetate, methyl isobutyl ketone, methyl propyl ketone, n-hexane, n-heptane, ethylene glycol monoethyl ether, ethylene glycol monoethylacetate, methylene dichloride, ethylene dichloride, propylene dichloride, carbon chloroform, nitroethane, nitropropane, tetrachloroethane, ethyl ether, isopropyl ether, cyclohexane, cyclo-octane, toluene, naphtha, 1,4-dioxane, tetrahydrofuran, diglyme, aqueous and nonaqueous mixtures thereof, such as acetone and water, acetone and methanol, acetone and ethyl alcohol, methylene dichloride and methanol, and ethylene dichloride and methanol.

DISCLOSURE OF EXAMPLES PROVIDED BY THE INVENTION

The following examples are merely illustrative of the present invention and they should not be considered as limiting the scope of the invention in any way. These examples and other equivalents thereof will become apparent to those versed in the art in the light of the present disclosure and the accompanying claims.

EXAMPLE 1

A therapeutic oxybutynin composition for administering to a patient and for use in the invention was prepared as follows: First, 103 grams of oxybutynin hydrochloride was dissolved in 1200 ml (milliliters) of anhydrous ethanol. Separately, 2,280 g of polyethylene oxide of 200,000 weight-average molecular weight, 150 g of hydroxypropylmethylcellulose of 9,200 average-number molecular weight and 450 g of sodium chloride were dry blended in a conventional blender for 10 minutes to yield a homogenous blend. Next, the oxybutynin ethanol solution was added slowly to the blend, with the blender continuously blending until all the ingredients were added to the three component dry blend, with the blending continued for another 8 to 10 minutes. The blended wet composition was passed through a 16 mesh screen and dried overnight at a room temperature of 72° F. (22.2°). Then, the dry granules were passed through a 20 mesh screen, 18 g of magnesium stearate was added, and all the ingredients blended again for 5 minutes. The fresh granules are ready for formulation into a therapeutic oxybutynin composition. The therapeutic composition comprises 3.4 wt % oxybutynin hydrochloride, 76 wt % polyethylene oxide of 200,000 weight-average molecular weight, 5 wt % of hydroxypropylmethylcellulose of 9,200 average-number molecular weight, 15 wt % sodium chloride, and 0.6 wt % magnesium stearate. The therapeutic composition can be administered for its intended oxybutynin therapy, the management of overactive bladder.

EXAMPLE 2

An osmopolymer hydrogel composition for use in the invention was prepared as follows: first 1274 g of pharmaceutically acceptable polyethylene oxide comprising a 7,500,000 weight-average molecular weight, 600 g of sodium chloride, and 20 g of colorant ferric oxide were separately screened through a 40 mesh screen. Then, all the screened ingredients were mixed with 100 g of hydroxypropylmethylcellulose of 11,200 average-number molecular weight to produce a homogenous blend. Next, 300 ml of denatured anhydrous alcohol was added slowly to the blend with continuous mixing for 5 minutes. Then, 1.6 g of butylated hydroxytoluene was added, followed by more blending, with 5 g of magnesium stearate added with 5 minutes of blending, to yield a homogenous blend. The freshly prepared granulation is passed through a 20 mesh screen and allowed to dry for 20 hours at 22.2° C. The final composition comprised 63.67 wt % polyethylene oxide of 7,500,000 weight-average molecualr weight, 30 wt % sodium chloride, 1 wt % ferric oxide, 5 mg hydroxypropylmethylcellulose of 11,200 average-number molecular weight, 0.08 wt % butylated hydroxytoluene, and 0.25 mg magnesium stearate.

EXAMPLE 3

An osmopolymer hydrogel composition for use in the invention was prepared as follows: first 1274 g of pharmaceutically acceptable sodium carboxymethylcellulose comprising a 2,250,000 weight-average molecular weight, 600 g of sodium chloride, and 20 g ferric oxide were separately screened through a 40 mesh screen. Then, all the screened ingredients were mixed with 100 g of hydroxypropylmethylcellulose of 11,200 average-number molecular weight and 100 g of hydroxypropylcellulose of 30,000 average-number molecular weight to produce a homogenous blend. Next, 300 ml of denatured anhydrous alcohol was added slowly to the blend with continuous mixing for 5 minutes. Then, 1.6 g of butylated hydroxytoluene was added, followed by more blending, with 5 g of magnesium stearate added with 5 minutes of blending, to yield a homogenous blend. The freshly prepared granulation was passed through a 20 mesh screen and allowed to dry for 20 hours at 22.2° C. The final composition comprised 58.67 wt % the sodium carboxymethylcellulose, 30 wt % sodium chloride, 1 wt % ferric oxide, 5 mg of hydroxypropylmethylcellulose, 5 mg hydroxypropylcellulose, 0.08 wt % butylated hydroxytoluene, and 0.25 mg of magnesium stearate.

EXAMPLE 4

The therapeutic oxybutynin composition and the osmopolymer hydrogel composition were made into a bilayered tablet as follows: first, 147 mg of the oxybutynin composition as prepared in Example 1 was added to a punch die set and tamped. Then, 98 mg of the hydrogel composition as prepared in Example 2 was added and the two layers compressed under a pressure head of 1.0 ton (1000 kg) into a $11/32$ inch (0.873 cm) diameter, contacting intimate bilayered tablet. The example was repeated with the hydrogel composition as prepared in Example 3 to produce the tablet comprising two layers.

EXAMPLE 5

The bilayered tablet for example as described in Example 4 was manufactured into a dosage form as follows: first, a semipermeable wall-forming composition was prepared comprising 95 wt % cellulose acetate having a 39.8% acetyl content, and 5 wt % polyethylene glycol having a number-average molecular weight of 3350 by dissolving the ingredients in a cosolvent comprising acetone and water in 90:10 wt:wt composition to make a 4% solid solution. The wall-forming composition was sprayed onto and around the bilayered cores as prepared in Examples 2 and 3 to provide a 26.4 mg semipermeable wall.

Next, the semipermeable walled, bilayered tablet was laser drilled to provide a 20 mil (0.51 mm) orifice to contact the oxybutynin layer and the exterior of the dosage form. The residual solvent was removed by drying for 48 hours at 50° C. and 50% relative humidity. Next, the dosage forms were dried further for 1 hour at 50° C. to remove excess moisture. The dosage form provided by this manufacture provides 3.4 wt % oxybutynin hydrochloride, 76 wt % polyethylene oxide of 200,000 weight-average molecular weight, 5 wt % hydroxypropylmethylcellulose of 9,200 average-number molecular weight, 0.6 wt % magnesium stearate, and 15 wt % sodium chloride in the therapeutic oxybutynin compositon. The osmopolymer hydrogel push composition comprises 63.67 wt % polyethylene oxide of 7,500,000 weight-average molecular weight, 30 wt % sodium chloride, 1 wt % ferric chloride, 5 wt % hydroxypropylmethylcellulose of 9,200 average-number molecular weight, 0.08 wt % butylated hydroxytoluene, and 0.25 wt % magnesium stearate. The semipermeable wall comprises 95 wt % cellulose acetate comprising 39.8% acetyl content, and 5 wt % polyethylene glycol of 3350 number-average molecular weight. The dosage form comprises an exit passage of 20 mils (0.50 mm) and it has a mean release rate of 0.260 mg/hr for 23.8 hours. The semipermeable wall provides substantial protection from photo (light) degradation of the oxybutynin in the dosage form.

EXAMPLE 6

A dosage form is prepared according to the above examples, comprising a drug layer comprising of 6.67 wt % oxybutynin hydrochloride, 87.83 wt % polyethylene oxide of 200,000 weight-average molecular weight, 4.00 wt % hydroxypropylmethylcellulose of 9,200 average-number molecular weight, and 0.50 wt % magnesium stearate; in layered contact with a push hydrogel layer comprising 58.75 wt % sodium carboxymethylcellulose of 6,000,000 weight-average molecular weight, 30 wt % sodium chloride, 5.00 wt % hydroxypropylmethylcellulose of 9,200 average-number molecular weight, 1.00 wt % ferric oxide, 5.00 wt % hydroxypropylcellulose of 75,000 average-number molecular weight and 0.25 wt % magnesium stearate; which bilayered core is surrounded by a semipermeable wall comprising cellulose acetate and polyethylene glycol; and an exit port through the wall for delivering the oxybutynin at a controlled rate over thirty hours.

EXAMPLE 7

The dosage form according to Example 6 wherein in the drug composition the polyethylene oxide has a 300,000 weight-average molecular weight; the hydroxypropylcellulose is a member selected from the group consisting of 25,000, 30,000, or 40,000 average-number molecular weight; and the dosage form comprises 5 mg to 250 mg of oxybutynin pharmaceutically acceptable salt.

EXAMPLE 8

A dosage form was prepared according to the above examples wherein the dosage form of this example comprises a drug oxybutynin layer comprising 5 mg oxybutynin, 111.60 mg polyethylene oxide of 200,000 weight-average molecular weight, 7.35 mg hydroxypropylmethylcellulose of 9,200 average-number molecular weight, 0.88 mg magnesium stearate, 22.05 mg of sodium chloride, and 0.12 mg of butylated hydroxytoluene; a hydrogel push layer comprising 62.40 mg of polyethylene oxide of 7,000,000 weight-average molecular weight, 29.40 mg of sodium chloride, 4.90 mg hydroxypropylmethylcellulose of 9,200 average-number molecular weight, 0.08 mg of butylated hydroxytoluene, 0.98 mg of red ferric oxide, and 0.24 mg of magnesium stearate; a wall comprising cellulose acetate consisting of a 39.8% acetyl content and polyethylene glycol of 3350 number-average molecular weight in the percentage ratio of 95 wt % celluloe acetate to 5 wt % polyethylene glycol, and exit means in the wall.

EXAMPLE 9

A dosage form was prepared according to the examples provided by this invention wherein the dosage form comprises: a drug anticholinergic oxybutynin layer comprising 5.3 wt % oxybutynin, 82.37 wt % polyethylene oxide of 200,000 weight-average molecular weight, 2 wt % hydroxypropylmethylcellulose of 9,200 average-number molecular weight, 0.25 wt % magnesium stearate, 10 wt % sodium chloride, and 0.08 wt % butylated hydroxytoluene; a push hydrogel layer comprising 63.37 wt % polyethylene oxide of 2,000,000 weight-average molecular weight, 30 wt % sodium chloride, 5 wt % hydroxypropylmethylcellulose of 9,200 average-number molecular weigh, 0.08 wt % butylated hydroxytoluene, 1 wt % black ferric oxide and 0.25 wt % magnesium stearate; a wall comprising 99 wt % cellulose acetate comprising a 39.8% acetyl content and 1 wt % polyethylene glycol of 3350 number-average molecular weight; and an exit passageway through the wall for delivering the oxybutynin to a patient, for treatment of symptoms in neurogenic bladder.

EXAMPLE 10

An oxybutynin compositon was prepared according to the above examples, wherein the composition comprises 10.6% oxybutynin hydrochloride, 79.57 wt % polyethylene oxide of 200,000 weight-average molecular weight, 2 wt % hydroxypropylmethylcellulose of 9,200 average-number molecular weight, 0.25 wt % of magnesium stearate, 7.5 wt % of sodium chloride, and 0.08 wt % butylated hydroxytoluene.

EXAMPLE 11

An oxybutynin composition was prepared according to the above examples wherein the composition comprises 16 wt % oxybutynin hydrochloride, 76.67 wt % polyethylene oxide of 200,000 weight-average molecular weight, 2 wt % hydroxypropylmethylcelluose of 9,200 average-number molecular weight, 0.25% magnesium stearate, 5 wt % sodium chloride, and 0.08 wt % butylated hydroxytoluene.

EXAMPLE 12

A hydrogel composition was prepared according to the above examples wherein the composition comprises 58.75 wt % hydroxyethylcellulose of 1,300,000 weight-average molecular weight, 30 wt % sodium chloride, 10 wt % polyvinylpyrrolidone of 42,000 viscosity-average molecular weight, 1 wt % colorant red ferric oxide, and 0.25 wt % magnesium stearate.

EXAMPLE 13

A dosage form was prepared according to the present invention wherein the dosage form comprises: a drug layer comprising 3.4 wt % oxybutynin hydrochloride, 76 wt % polyethylene oxide of 200,000 weight-average molecular weight, 5 wt % hydroxypropylmethylcellulose of 9,200 average-number molecular weight, 0.6 wt % magnesium stearate, 15 wt % sodium chloride, a push hydrogel layer comprising 58.75 wt % hydroxyethylcellulose of 1,300,000 average-number molecular weight, 30 wt % sodium chloride, 10 wt % polyvinylpyrrolidone of 42,000 viscosity-average molecular weight, 1 wt % red ferric oxide, and 0.25 wt % magnesium stearate; a wall comprising 95 wt % cellulose acetate comprising a 39.8% acetyl content, and 5 wt % polyethylene glycol of 3350 number-average molecular weight, an exit orifice of 20 mil (0.50 mm); and a release rate of 0.292 mg per 1 hour for 16.9 hours.

EXAMPLE 14

A dosage form was manufactured according to the present examples wherein the dosage form comprises: a drug oxybutynin composition comprising 3.4 wt % oxybutynin hydrochloride, 76 wt % polyethylene oxide of 200,000 weight-average molecular weight, 5 wt % hydroporpylmethylcellulose of 9,200 average-number molecular weight, 0.6 wt % of magnesium stearate, and 15 wt % sodium chloride; a push hydrogel composition for pushing the drug oxybutynin composition form the dosage form comprising 63.67 wt % polyethylene oxide of 7,000,000 weight-average molecular weight, 30 wt % sodium chloride, 1 wt % red ferric oxide, 5 wt % hydroxypropylmethylcellulose of 9,200 average-number molecular weight, 0.08 wt % butylated hydroxytoluene, and 0.25 wt % magnesium stearate; a subcoat that surrounds the drug oxybutynin composition and push hydrogel composition wherein the subcoat comprises 95 wt % hydroxyethylcellulose, a nonionic water soluble polymer of 90,000 average-number molecular weight; then an outer wall or overcoat comprising 95 wt % cellulose acetate possessing an acetyl content of 39.8% and 5 wt % polyethylene glycol of 3,350 number-average molecular weight; a 20 mil (0.50 mm) exit passageway; and an oxybutynin release rate of 0.295 mg per 1 hour over 19.9 hours.

EXAMPLE 15

A dosage form designed and shaped as a pharmaceutically acceptable tablet for the oral administration of a member selected from the group consisting of oxybutynin and its pharmaceutically acceptable salts was made by following the above examples. The dosage form provided by the example comprises a drug composition weighing 92 mg comprising 5.45 wt % of oxybutynin hydrochloride, 9.98 wt % of sodium chloride, 82.16 wt % of polyethylene oxide of 100,000 of weight-average molecular weight, 2.00 wt % of hydroxypropylmethylcellulose of 11,300 of average-number molecular weight, 0.25 wt % of magnesium stearate, 0.08 wt % of butylated hydroxytoluene, and 0.05 wt % of green ferric oxide. The composition was surrounded by a wall comprising a semipermeable cellulose acetate polymer comprising a 39.8% acetyl content and polyethylene glycol comprising a 3,350 molecular weight. The dosage form comprised an exit in communication with the oxybutynin composition for delivering oxybutynin to the gastrointestinal tract of a patient.

EXAMPLE 16

A dosage form adapted as an orally administrable caplet was made according to the above examples. The dosage form of this example comprises a drug composition weighing 92 mg and comprising 5.45 wt % oxybutynin hydrochloride, 9.98 wt % sodium chloride, 82.19 wt % polyethylene oxide possessing a 200,000 weight-average molecular weight, 2.00 wt % hydroxypropylmethylcellulose of 11,300 molecular weight, 0.25 wt % magnesium stearate, 0.08 wt % butylated hydroxytoluene, and 0.05 wt % colorant green ferric oxide; a push composition initially in contact with the drug composition, weighing 62 mg and comprising 63.67 wt % polyethylene oxide possessing a 2,000,000 weight-average molecular weight, 30.00 wt % sodium chloride, 5.00 wt % hydroxypropylmethylcellulose of 11,200 molecular weight, 1.00 wt % of a 95.5 mixture of colorant black iron oxide/lactose, 0.25 wt % magnesium stearate, and 0.08 wt % butylated hydroxytoluene; a wall weighing 19 mg that surrounds the compositions and comprises 99 wt % of cellulose acetate of 39.8% acetyl content, and 1.00 wt % polyethylene glycol of 3,350 molecular weight; a yellow color overcoat weighing 10 mg; and an exit in the wall for delivering the drug to a patient. The dosage form exhibited a cumulative release of oxybutynin hydrochloride of greater than zero mg to 1 mg in 0 to 4 hours, 1 mg to 2.5 mg in 0 to 8 hours, 2.75 mg to 4.25 mg in 0 to 14 hours, and 3.75 mg to 5 mg in 0 to 24 hours.

EXAMPLE 17

A dosage form for the oral administration of oxybutynin was made by following the above examples. The dosage form comprises a 92 mg drug composition comprising 10.90 wt % oxybutynin hydrochloride, 7.48 wt % sodium chloride, 79.25 wt % polyethylene oxide possessing a 200,000 weight-average molecular weight, 1.99 wt % hydroxypropylmethylcellulose possessing a 11,300 molecualr weight, 0.25 wt % magnesium stearate, 0.08 wt % butylated hydroxytoluene, and 0.25 wt % magnesium stearate, 0.08 wt % butylated hydroxytoluene, and 0.05 wt % colorant red ferric oxide; a push composition weighing 62 mg and comprising 63.67 wt % polyethylene oxide possessing a 2,000,000 weight-average molecular weight, 30 wt % sodium chloride, 5 wt % hydroxypropylmethylcellulose possessing a 11,300 molecular weight, 1.00 wt % colorant black iron oxide/lactose (95:5), 0.25 wt % magnesium stearate, and 0.08 wt % butylated hydroxytoluene; a semipermeable wall that envelopes the compositions weighting 19 mg comprising 99 wt % cellulose acetate comprising a 39.8 acetyl content, and 1 wt % polyethylene gylcol 3350; a exit in the wall; and a 10 mg color overcoat. The dosage form, when in operation operates by osmotic kinetics, and delivers in 0 to 4 hours up to 20% (up to 2 mg) of oxybutynin hydrochloride, in 0 to 8 hours 20 to 50% (2.0 to 5.0 mg) of oxybutynin salt; in 0 to 14 hours 50 to 85% (5.5 mg to 8.5 mg) of oxybutynin; and 0 to 24 hours greater than 75% (greater than 7.5 mg) of the drug. The dosage form can be manufactured shaped like a pharmaceutically acceptable tablet, or the dosage form can be manufactured shaped like a pharmaceutically acceptable capsule.

EXAMPLE 18

A dosage form for the oral delivery of a member selected from the group consisting of oxybutynin and its pharmaceutically acceptable salts was made according to the above examples. The dosage form comprised a drug composition weighing 92 mg comprising 16.30 wt % oxybutynin chloride, 4.98 wt % sodium chloride, 76.35 wt % polyethylene oxide of 200,000 molecular weight, 1.99 wt % hydroxypropylmethylcellulose, 0.25 wt % magnesium stearate, 0.08 wt % butylated hydroxytoluene, 0.02 wt % black iron oxide/lactose (95:5); a push composition weighing 62 mg comprising 63.67 wt % polyethylene oxide possessing a 2,000,000 molecular weight, 30.00 wt % sodium chloride, 5.00 hydroxypropylmethylcellulose of 11,300 molecular weight, 1.00 wt % black iron oxide/lactose (95:5), 0.25 wt % magnesium stearate, and 0.08 wt % butylated hydroxytoluene; a wall weighing 19 mg comprising a semipermeable composition permeable to a fluid flux, impermeable to drug flux comprising 99.00 wt % cellulose acetate having a 39.8 acetyl content, and 1.00 wt % polyethylene glycol 3350; a passageway in the wall; and a overcoat weighing 10 mg colored grey. The dosage form exhibited a cumulative release rate of up to 3 mg in 0 to 4 hours; 3 mg to 7.5 mg in 0 to 8 hours; 8 mg to 13 mg in 0 to 14 hours; and 12 mg to 15 mg in 0 to 24 hours.

EXAMPLE 19

A dosage form was prepared according to the previous examples comprising an oxybutynin salt, that delivers up to 1.60 mg in 0 to 4 hours, up to 5 mg in 0 to 8 hours, up to 8.5 mg in 0 to 12 hours, up to 11 mg in 0 to 16 hours, and up to 15 mg in 0 to 24 hours.

EXAMPLE 20

An orally administrable dosage form comprising 1 mg to 100 mg of a drug selected from the group consisting of oxybutynin and its pharmaceutically acceptable salt is prepared by following the previous examples, for administering accompanied by a different drug, or prior to or after the administration of conjugated equine estrogens.

EXAMPLE 21

A dosage form is prepared according to the above examples wherein the dosage form of this example comprises a drug oxybutynin steroid composition comprising 5 mg oxybutynin, 0.3 mg conjugated estrogens, 111.60 mg polyethylene oxide of 200,000 weight-average molecular weight, 7.35 mg hydroxypropylmethylcellulose of 9,200 average-number molecular weight, 0.88 mg magnesium stearate, 22.05 mg of sodium chloride, and 0.12 mg of butylated hydroxytoluene; a hydrogel push composition comprising 62.40 mg of polyethylene oxide of 7,000,000 weight-average molecular weight, 29.40 mg of sodium chloride, 4.90 mg hydroxypropylmethylcellulose of 9,200 average-number molecular weight, 0.08 mg of butylated hydroxytoluene, 0.98 mg of red ferric oxide, and 0.24 mg of magnesium stearate; a wall comprising cellulose acetate consisting of a 39.8% acetyl content and polyethylene glycol of 3350 number-average molecular weight in the percentage ratio of 95 wt % cellulose acetate to 5 wt % polyethylene glycol, and an exit passageway in the wall.

EXAMPLE 22

A dosage form is prepared according to the previous example, wherein the dosage form comprises a drug composition comprising oxybutynin in a dose of 5 mg to 20 mg of oxybutynin and at least one of a steroid member selected from the dose group consisting of 0.3 mg, 0.625 mg, 0.9 mg, 1.25 mg and 2.5 mg of a mixture of estrogen sulfates, estrone, equilin, 17α-dihydroequilin, 17α-estradiol, equilenin and 17α-dihydroequilenin indicated for treating urge incontinence, the symptoms associated with menopause, and hormone replacement therapy.

EXAMPLE 23

A bioerodible dosage form is prepared comprising a bioerodible polymer in matrix dosage form comprising 5 mg of oxybutynin and 0.3 mg of an estrogen that provides for the drugs release at controlled rate by the bioeroding matrix over 24 hours. The bioerodible polymer forming the dosage form matrix comprises a member selected from the group consisting of poly(ester), poly(amine), poly(lactide), poly(glycolide), poly(lactide-co-glycolide), poly(caprolactone), poly(hydroxybutynin acid), poly(orthoester), poly(orthocarbonate), poly(dihydropyran), poly(3-hydroxybutyrate-co-3-hydroxyvalerate), and poly(3-hydroxybutyrate-co-hydroxybutyrate). An additional dosage form can be prepared according to the example that administers a member selected from oxybutynin and its pharmaceutically acceptable salt and 30 μg ethinyl estradiol and 150 μg of levonorgestrel.

EXAMPLE 24

A diffusion rate-controlled dosage form that comprises a diffusion-rate controlled polymer through which oxybutynin and a steroid is released by diffusion is prepared by formulating oxybutynin and a member selected from the group consisting of a progestin and estrogen pair, and an estrogen, in a polymer matrix. The diffusion can be through the polymer or through a porous-polymer membrane. The diffusion dosage form structurally includes a polymer matrix that is a reservoir for the drug(s), or through a contacting polymer rate-governing membrane. Representative of polymers for providing diffusional dosage forms comprise a member selected from the group consisting of poly(olefin), poly(vinyl), poly(carbohydrate), poly(peptide), poly(condensation), poly(rubber), and poly(silicon). Representative of specific polymers consists of a member selected from the group consisting of poly(ethylene), poly(propylene), copoly(ethylene-vinyl acetate), poly(isobutylethylene), poly(vinylaurate), cross-linked poly(vinylalcohol), poly(methacrylate), poly(amide), poly(ester), and poly(silicone).

EXAMPLE 25

A dosage form comprising ion-exchange activity is prepared and it comprises a water-insoluble crosslinked polymer with oxybutynin and estrogen bound to the ion-exchange resin. The drugs are released at a rate controlled by the drug-resin complex by the ionic environment within the gastrointestinal tract. The ion-exchange resins that can be adapted for the manufacture of the dosage form comprise a cation-exchange resin and an anion-exchange resin. The cation-exchange resins include strong-acid and weak-acid resins as with sulfonic acid, carboxylic acid, and phosphonic acid and the anion-exchange resins include strong-base and weak-base resins as with quaternary ammonium, secondary amine, tertiary amine aromatic and tertiary amine aliphatic resins. Specific examples of ion-exchange resins such as Amberlite IR-120, basic ion-exchange resins such as Amberlite IRA-400, weak basic ion-exchange resins such as Amberlite IR-45.

EXAMPLE 26

A method of manufacturing a sustained release dosage form for managing the concentration of oxybutynin and its desethylmetabolite in plasma, is provided, which method of manufacture comprises the incorporation of an effective amount of oxybutynin or its pharmaceutically acceptable salt in a sustained and controlled release dosage form which release oxybutynin continuously at a controlled zero order rate to provide a relatively higher oxybutynin concentration and a relatively lower desethylmetabolite concentration than provided by an immediate release non-sustained dosage form profile.

METHOD OF PRACTICING THE INVENTION

The drug oxybutynin, identified as OXY, was administered in a clinical study to a number of patients to treat urinary incontinence. Patients who self-administered oxybutynin often quit or discontinue treatment due to its anticholinergic side effects, which appear to be peak-concentration related. The present invention thus provides a sustained release (SR) controlled-release (CR) oral dosage form comprising oxybutynin designed to provide both oxybutynin therapy through the entire gastrointestinal tract and a continuous plasma drug concentration that avoid peak and valley concentrations. The sustained release dosage form of this invention continuously delivers oxybutynin throughout the entire gastrointestinal tract (GI), thereby making its therapeutically effective for oxybutynin to be absorbed throught the entire gastrointestinal tract into the blood. That is, the controlled-extended release dosage form of this invention maintains a therapeutic plasma concentration substantively free of an overdose and substantially free of an ineffective underdose of oxybutynin.

In a multiple dose, crossover study, 13 healthy female volunteers of 41 to 68 years of age received either 5 mg of oxybutynin immediate release (IR) every 8 hours, or three 5 mg controlled release (CR) once a day, for four days. The patients blood was sampled on days 1 and 4 to quantify oxybutynin and its desethylmetabolite (DESOXY) by liquid chromatography mass spectroscopy (LC/MS). The oxybutynin was absorbed rapidly following immediate-release (IR) dosing with a mean $C_{max}$ of ng/ml. $C_{max}$ is the maximum concentration after dosing in the plasma. The drug release kinetics for the controlled-release (CR) plasma concentration rose slowly, reaching a mean $C_{max}$ value of 4.2–6.7 ng/ml. The metabolite DESOXY was formed rapidly following immediate release, and its formation paralleled the slow absorption of oxybutynin following controlled release. The DESOXY had a shorter $t_{1/2}$ life compared to OXY, indicating presystemic metabolite formation assuming it to be true metabolite $t_{1/2}$. Single and multiple dose AUC values were similar for both the controlled release and immediate release suggesting time invariant pharmacokinetics. AUC denotes the area under the plasma concentration profile. The 4 day OXY and DESOXY AUC and their ratios are presented in the Table below wherein BA denotes the percent bioavailable, that is, BA denotes the relative amount of oxybutynin absorbed from the controlled release (CR) dosage form compared to the immediate release (IR) dosage form, and $C_{max}$ denotes the maximum concentration.

|    | OXY(AUC) (ng · h/mL) | DESOXY (AUC) (ng · h/mL) | OXT/DESOXY Ratio | OXY (BA %) | DESOXY (BA %) |
|----|----------------------|--------------------------|------------------|------------|---------------|
| IR | 81                   | 483                      | 0.18             |            |               |
| CR | 109                  | 304                      | 0.41             | 153        | 69            |

The higher ratio of OXY-BA following CR compared to IR suggests lower metabolic formation on first pass. This indicates CR could reach the colon within 3–5 hours post dosing. Presystemic cytochrome P450-mediated oxidation may occur in the upper part of the gastrointestinal tract; then, drug release from CR in the colon escapes presystemic metabolism, which could explain the higher OXY/DESOXY ratio and increased OXY BA following CR.

The dosage form and the oxybutynin composition of this invention, as seen from the above disclosure, can be used in a method for administering a drug by the oral route, or the dosage form and composition can be sized and shaped for administering a drug by the sublingual and buccal routes. The sublingual and buccal routes can be used for quicker therapy, and they can be used when a smaller dose of drug is needed for immediate therapy. The latter routes can be used as a by-pass of the first pass of hepatic metabolism of the drug.

In summary, it will be appreciated that the present invention contributes to the art an unobvious dosage form that possesses practical therapeutic utility, and it can administer a drug at a dose-metered release rate per unit time.

We claim:

1. A method for the management of incontinence in a patient, wherein the method comprises admitting orally into the patient a dosage form comprising 240 ng to 650 mg a member selected from the group consisting of oxybutynin and its pharmaceutically acceptable salt, that is administered once-a-day at a release rate of 0.05 mg per hour up to 0.850 mg per hour for the management of incontinence in the patient.

2. The method for the management of incontinence in a patient according to claim 1, wherein the dosage form is a sustained-release dosage form and the pharmaceutically acceptable salt is a member selected from the group consisting of acetate, bitartrate, citrate, edetate, chloride, edisylate, estolate, esylate, fumarat, , gluceptate, gluconate, glutamate, bromide, lactate, malate, maleate, mandelate, mesylate, methyinitrate, mucate, napsylate, nitrate, pamoate, pantothenate, phosphate, salicylate, stearate, succinate, sulfate, tannate, and tartrate.

3. The method for the management of incontinence in a patient according to claim 1, wherein the dosage form is a controlled-release dosage form and the oxybutynin is present as a racemate.

4. The method for the management of incontinence in a patient according to claim 1, wherein the dosage form is a member selected from the group consisting of a tablet, capsule, caplet, bead, and matrix and the oxybutynin is present as the R-enantiomer.

5. The method for the management of incontinence in a patient according to claim 1, wherein the dosage form is a member selected from the group consisting of a tablet, capsule, caplet, bead and matrix and the oxybutynin is present as the S-enantiomer.

6. A method for treating incontinence in a patient exhibiting the symptoms of incontinence, wherein the method comprises admitting orally into the patient a sustained release dosage form comprising 240 ng to 650 mg of a member selected from the group consisting of oxybutynin and its pharmaceutically acceptable salt that is administered once-a-day at a incontinence-managing rate of 10 ng per hour to 20 mg per hour for the management of incontinence.

7. The method for treating incontinence in a patient according to claim 6, wherein the method administers the pharmaceutically acceptable salt oxybutynin chloride over 24 hours.

8. A method for the management of incontinence and for the management of hormone replacement therapy in a patient, wherein the method comprises administering once-a-day a sustained-release therapeutically effective dose of a member selected from the group consisting oxybutynin and its pharmaceutically acceptable salt for the management of incontinence, and administering a therapeutically effective dose of an estrogenic steroid for the management of hormone replacement therapy to the patient in need of both therapies.

9. The method for the management of incontinence and for the management of hormone replacement therapy according to claim 8, wherein the oxybutynin and the estrogenic steroid are administered at the same time.

10. The method for the management of incontinence and for the management of hormone replacement therapy according to claim 8, wherein a progestin is administered with the estrogenic steroid.

11. The method for the management of incontinence and for the management of hormone replacement therapy according to claim 8, the oxybutynin and the estrogenic steroid are administered at a different time.

12. The method for the management of incontinence and for the management of hormone replacement therapy according to claim 8, wherein the administration of the estrogenic steroid is accompanied by the administration of a progestin steroid as a steroid pair and at a different time from the administration of the oxybutynin.

13. The method for the management of incontinence and for hormone replacement therapy according to claim 8, wherein the estrogenic steroid is a conjugated equine estrogen.

14. A method for treating involuntary incontinence in a patient, wherein the method comprises admitting orally into the patient a sustained release once-a-day dosage form comprising 240 ng to 650 mg of a member selected from the group consisting of oxybutynin and its pharmaceutically acceptable salt, that is administered in a sustained rate to provide in the plasma of the patient a higher oxybutynin/desethylmetabolite ratio than about 0.18 to 1 for treating involuntary incontinence in the patient.

15. A method for managing the concentrations of oxybutynin (OXY) and its desethylmetabolite (DESOXY) in the plasma of a patient, and for managing incontinence in the patient, wherein the method comprises admitting orally into the patient a once-a-day dosage form comprising 240 ng to 650 mg of a member selected from the group consisting of oxybutynin and its pharmaceutically acceptable salt, that is administered at a controlled rate to provide higher OXY/DESOXY ratio than about 0.18 to 1 for managing the plasma concentrations and for managing incontinence in the patient.

16. A method for the management of overactive bladder and for increasing compliance in a patient in need of said management and compliance wherein the method comprises admitting orally into the patient a once-a-day dosage form comprising 240 ng to 650 mg of a member selected from the group consisting of oxybutynin and its pharmaceutically acceptable salt that is administered in a sustained-release dosage of 0.10 ng per hour to 25 mg per hour for increasing patient compliance for the management of overactive bladder in the patient.

17. The method according to claim 16, wherein the dosage form comprises a polymer selected from the group consisting of an erodible, nonerodible, diffusion, ion-exchange, and porous polymers.

18. The method according to claim 16, wherein the dosage form is an osmotic dosage form.

19. The method according to claim 16, wherein the dosage form comprises tiny pills.

20. The method according to claim 16, wherein the patient is administered a member selected from the group consisting of an estrogen and a progestin.

21. The method according to claim 16, wherein the dosage form comprises drug releasing beads.

22. A method for treating an overactive bladder in a female patient, wherein the method comprises admitting orally once-a-day into the patient a dosage form comprising 240 ng to 650 mg a member selected from the group consisting of oxybutynin and its pharmaceutically acceptable salt that is administered once-a-day in a controlled release dose of 0.05 mg per hour to 0.850 mg per hour for treating the overactive bladder in the female patient.

23. The method for treating the overactive bladder according to claim 22, wherein the dosage form comprises a member selected from the group consisting of poly(amide), poly(amino acid), poly(ester), poly(lactic acid), poly(glycolic acid), poly(orthoester), poly(orthocarbonate), poly(acetyl), poly(anhydride), poly(dehydropyran), poly(carbohydrate), and poly(dioxinone).

24. The method for treating the overactive bladder according to claim 22, wherein the dosage form comprises a member selected from the group consisting of an olefin, vinyl, condensation, addition, carbohydrate, and silicon polymer.

25. The method for treating the overactive bladder according to claim 22, wherein the dosage form comprises a member selected from the group consisting of hydroxypropylalkylcellulose, and hydroxyalkylcellulose.

26. The method for the management of overactive bladder and hormone replacement therapy in a female patient, wherein the method comprises orally administering once-a-day to the patient a member selected from a group consisting of oxybutynin and its pharmaceutically acceptable salt at a therapeutically-effective, sustained release rate for the management of the overactive bladder, and orally administering to the patient a composition comprising a therapeutically-effective amount of a steroid selected from the group an estrogen and a progestin for hormone replacement therapy.

27. The method for the management of overactive bladder and hormone replacement therapy according to claim 26 wherein the oxybutynin and the steroid are administered at the same time.

28. The method for the management of overactive bladder and hormone replacement therapy according to claim 26, wherein the oxybutynin and the steroid are administered at different times.

29. The method for the management of overactive bladder and hormone replacement therapy according to claim 26, wherein the estrogen is a member selected from the group consisting of estradiol, estradiol valerate, estradiol benzoate, estradiol cypionate, estradiol propionate, estradiol dipropionate, estradiol acetate, ethinyl estradiol, 17α-ethinyl estradiol, 17α-ethinyl estradiol esters, 17α-ethinyl estradiol acetate, 17α-ethinyl estradiol benzoate, 17α-ethinyl estradiol ethers, estrone, estrone acetate, estrone sulfate, estriol, estriol succinate, estriol triacetate, conjugated equine estrogens, and estradiol esters.

30. The method for the management of overactive bladder and hormone replacement therapy according to claim 26, wherein the progestin is a member selected from the group consisting of progesterone, medroxyprogesterone, medroxyprogesterone acetate, hydroxyprogesterone, hydrogesterone caproate, norethindrone, norethindrone acetate, megestrol, megestrol acetate, progestin, progestogin, norgestrel, norethisterone, norethisterone acetate, levonorgestrel, norgestimate, norethynodrel, 17-hydroxyprogesterone esters, 19-nor-17-hydroxyprogesterone, 19-nor-17-hydroxyprogesterone esters, 17α-ethinyltestosterone, 17α-ethinyl-19-nor-testosterone, d-17β-acetoxy- 13β-ethyl-17α-ethinyl-17β-hydroxygon-4-en-3-one, 13β-ethyl-17β-hydroxygon-4-en-3-one, 13β-17α-diethyl-17β-hydroxygon-4-en-3-one, chlormadione acetate, dimethistrone, 17α-ethinyl-β-acetoxy-19-norandrost-4-en-3-one oxime, 3-ketodesogestrel, desogestrel, gestodine, and gestodene acetate.

31. The method for the management of overactive bladder and hormone replacement therapy according to claim 26, wherein the oxybutynin is administered from a dosage form selected from the group consisting of osmotic, diffusion, erodible, nonerodible, and ion-exchange dosage forms.

* * * * *

UNITED STATES PATENT AND TRADEMARK OFFICE
Certificate

Patent No. 6,262,115 B1                                                                                             Patented: July 17, 2001

On petition requesting issuance of a certificate for correction of inventorship pursuant to 35 U.S.C. 256, it has been found that the above identified patent, through error and without any deceptive intent, improperly sets forth the inventorship.

Accordingly, it is hereby certified that the correct inventorship of this patent is: George V. Guittard, Cupertino, CA (US); Francisco Jao, San Jose, CA (US); Susan M. Marks, San Jose, CA (US); David J. Kidney, Palo Alto, CA (US); Fernando E. Gumucio, San Jose, CA (US); Suneel Gupta, Sunnyvale, CA (US); and Gayatri Sathyan, San Jose, CA (US).

Signed and Sealed this Seventeenth Day of October 2006.

JOHANN RICHTER
*Supervisory Patent Examiner*
Art Unit 1616